(12) United States Patent
Montanari et al.

(10) Patent No.: US 6,645,396 B2
(45) Date of Patent: Nov. 11, 2003

(54) HYDROGEN GETTER COMPOSITION

(75) Inventors: Fernando Montanari, Milan (IT); Silvio Quici, Milan (IT); Amedea Manfredi, Milan (IT); Elena Villa, Milan (IT); Serena Della Bianca, Passirana di Rho (IT); Luca Toia, Carnago (IT)

(73) Assignee: SAES Getters S.p.A., Lainate (IT)

( * ) Notice: Subject to any disclaimer, the term of this patent is extended or adjusted under 35 U.S.C. 154(b) by 0 days.

(21) Appl. No.: 10/244,906

(22) Filed: Sep. 16, 2002

(65) Prior Publication Data

US 2003/0052304 A1 Mar. 20, 2003

Related U.S. Application Data

(63) Continuation of application No. PCT/IT01/00105, filed on Mar. 2, 2001.

(30) Foreign Application Priority Data

Mar. 15, 2000 (IT) ........................ MI2000A0529

(51) Int. Cl.[7] .................. H01J 7/18; C09K 3/00; C07D 251/00
(52) U.S. Cl. ................ 252/181.1; 252/181.6; 544/219
(58) Field of Search ........................ 544/219

(56) References Cited

U.S. PATENT DOCUMENTS

| | | |
|---|---|---|
| 3,896,042 A | 7/1975 | Anderson et al. |
| 4,405,487 A | 9/1983 | Harrah et al. |
| 4,616,014 A | 10/1986 | Teraji et al. |
| 5,624,598 A | 4/1997 | Shepodd et al. |
| 5,703,378 A | 12/1997 | Shepodd et al. |

FOREIGN PATENT DOCUMENTS

WO    W/O 99/63298 A1    12/1999

*Primary Examiner*—Matthew A. Thexton
(74) *Attorney, Agent, or Firm*—Akin, Gump, Strauss, Hauer & Feld, L.L.P.

(57) ABSTRACT

The present invention relates to a composition capable of hydrogen sorption in a closed container at low pressure, comprising an unsaturated organic substance and a hydrogenation catalyst. Said unsaturated organic substance is a compound having general formula A or A', or a dimer or polymer thereof, or a copolymer wherein one of the structural units has the general formula A or A':

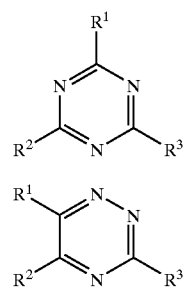

wherein $R^1$, $R^2$ and $R^3$ are hydrogen or hydrocarbon moieties optionally comprising one or more heteroatoms, at least one among $R^1$, $R^2$ and $R^3$ being chosen in the group of alkenyl, alkynyl, arylalkenyl and arylalkynyl moieties, optionally comprising one or more heteroatoms.

6 Claims, 2 Drawing Sheets

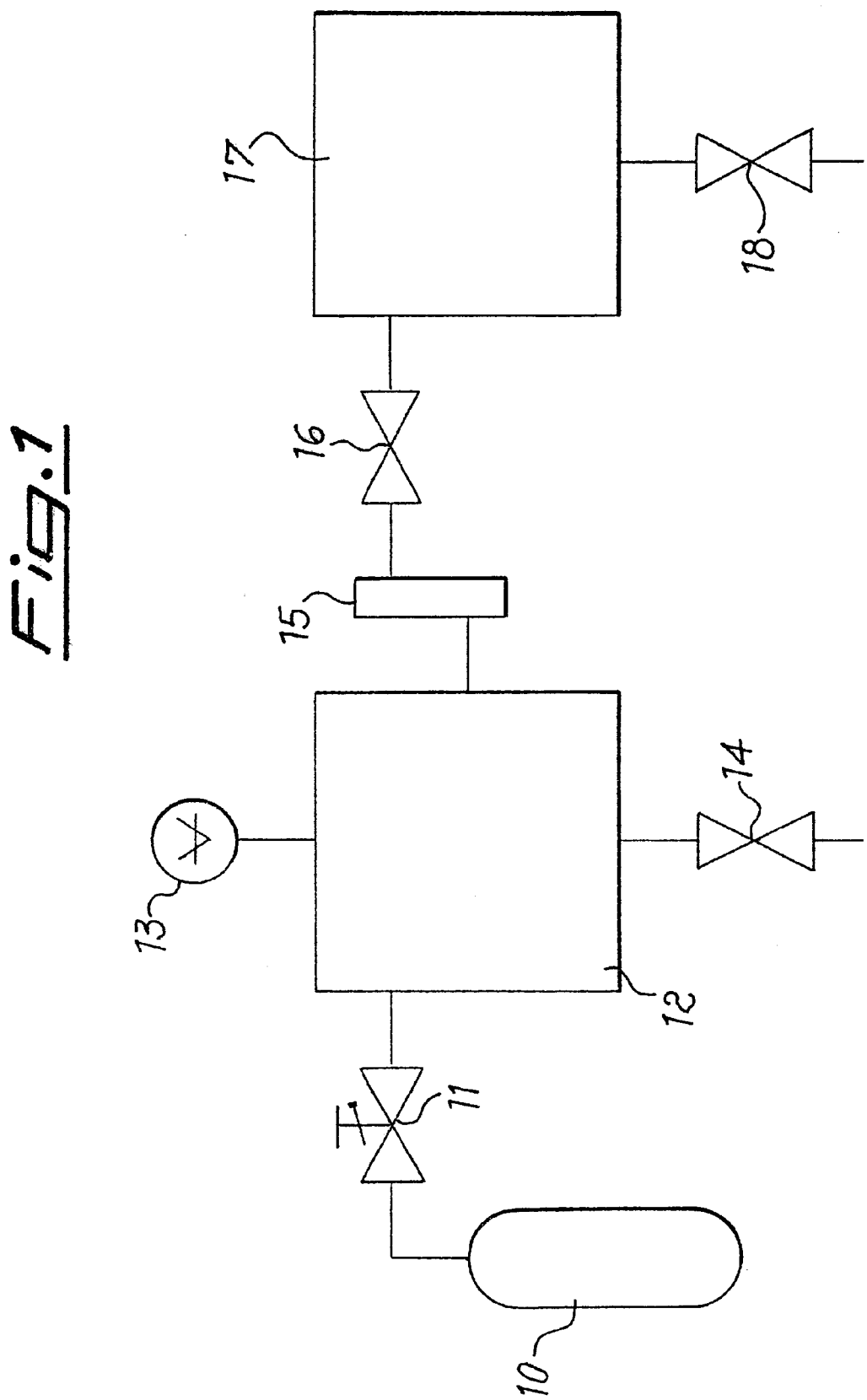

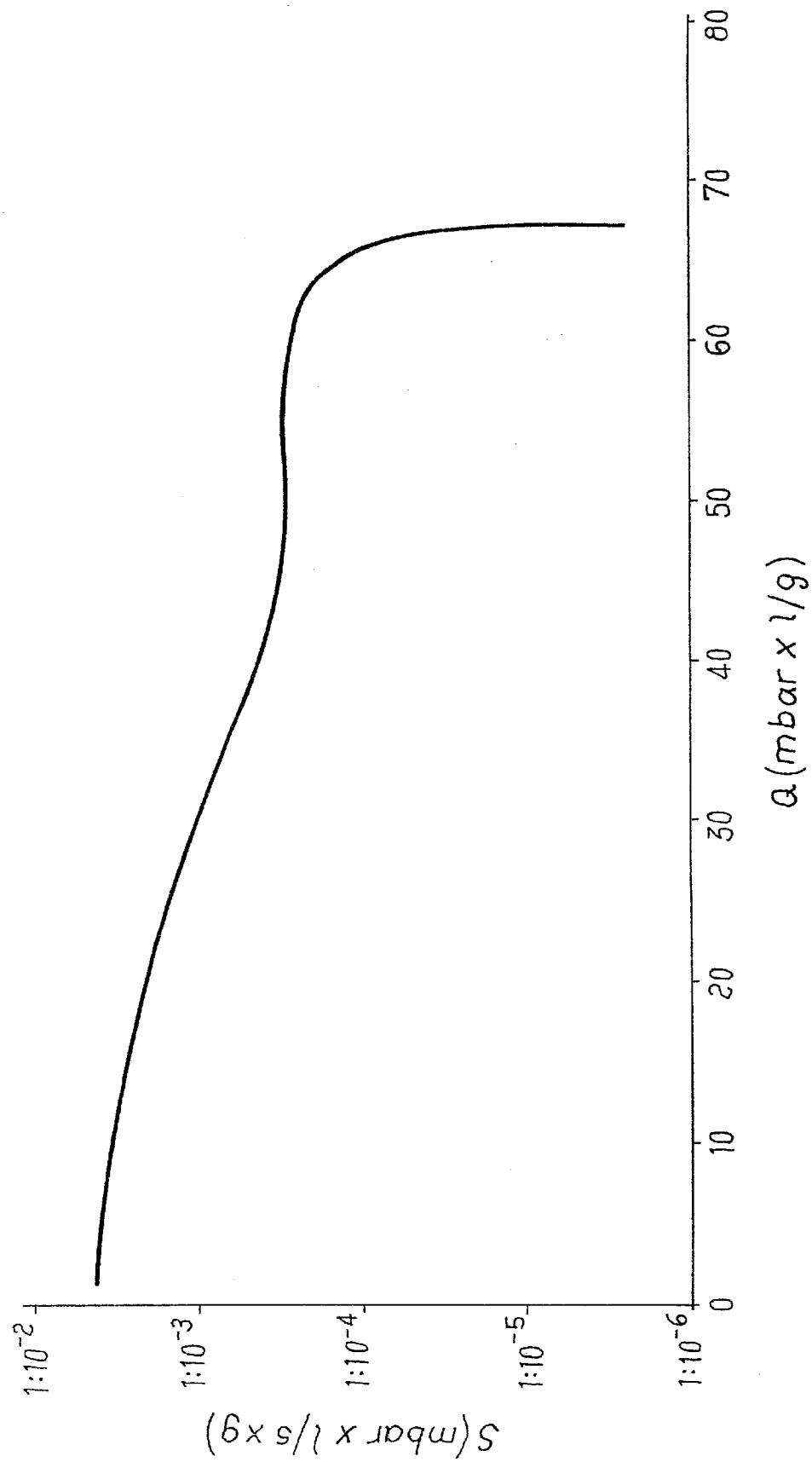

HYDROGEN GETTER COMPOSITION

CROSS-REFERENCE TO RELATED APPLICATIONS

This application is a continuation of International Application No. PCT/IT01/00105, filed Mar. 2, 2001, which was published in the English language on Sep. 20, 2001, under International Publication No. WO 01/68516 A1 and the disclosure of which is incorporated herein by reference.

BACKGROUND OF THE INVENTION

The present invention relates to a composition capable of hydrogen sorption in a closed container at low pressure, and particularly it relates to a composition formed of an unsaturated organic substance and a hydrogenation catalyst.

Getter materials have been in use for a long time in all the industrial applications which require the vacuum maintenance in a closed system. A particularly important application uses the property of low thermal conductivity of the vacuum for realizing thermal insulation systems for any material or device. Said insulation is generally obtained by creating, outside the material or device to be insulated, a double wall with evacuated interspace.

Since hydrogen has, among gases, the largest thermal conductivity, it is particularly important to provide means for sorbing the traces of hydrogen which are still present in the evacuated interspaces so as to complete the achievement of vacuum. Furthermore, due to the small size of the hydrogen molecule, this gas outgases very easily from the walls of the evacuated containers and has to be continuously sorbed in order to maintain the thermal insulation property.

It is known that the organic compounds comprising unsaturated bonds among carbon atoms react with hydrogen in the presence of a suitable catalyst being converted into the corresponding saturated compounds. By virtue of this reactivity, said compounds, combined with a suitable catalyst, can be advantageously used as hydrogen getters.

Although in principle all compounds comprising a double or triple bond between two carbon atoms can sorb hydrogen, some fundamental requirements have to be satisfied for a compound to be industrially used. A first requirement relates to the specific rate of the reaction with hydrogen, which has to be high in order to avoid an accumulation of hydrogen in closed systems. Furthermore, it is necessary that said hydrogenation reaction be capable of occurring also at very low partial hydrogen pressures, in other words that the equilibrium of the reaction be shifted towards the products. Another requirement, important for ensuring that the unsaturated compound remains on the catalyst, is that said unsaturated compound have a low vapor pressure within the whole range of working pressure and temperature.

U.S. Pat. No. 3,896,042 discloses a method for sorbing hydrogen from a closed system at low pressure and low temperature, which consists in placing inside said container a hydrogenation catalyst suitably supported on an inert substrate and coated with an unsaturated organic compound. The unsaturated organic compounds described in said patent are some arylacetylenes and particularly dimerized propargyl phenyl ether, dimerized benzylacetylene, dimerized phenylpropiolate, dimerized diphenyl propargyl ether and polydipropargyl ether of bisphenol-A.

U.S. Pat. No. 4,405,487 describes a combination of getter materials, which can be used for instance inside sealed containers for electronic and mechanical components, comprising a moisture getter and a hydrogen getter. The latter is formed of a hydrogenation catalyst and of a solid acetylenic hydrocarbon, comprising no nitrogen and sulphur heteroatoms. In fact, according to the patent teaching, these elements can bring about the generation of undesired by-products by hydrolysis. The acetylenic hydrocarbon which is indicated as particularly advantageous also from the point of view of the hydrogenation rate and of the hydrogen gettering capacity per gram of compound is 1,4-diphenylbutadiyne.

U.S. Pat. No. 5,624,598 and U.S. Pat. No. 5,703,378 describe a composition for hydrogen sorption at low pressures and high temperatures, which can be used for instance for thermal insulation of the pipes for transportation of high temperature fluids. Said composition is formed of a suitable catalyst and of a hydrocarbon compound, or polymer, comprising triple bonds between carbon atoms and aromatic moieties selected among benzene, styrene, naphthalene, anthracene, diphenyl, fluorene, phenanthrene and pyrene. The presence of aromatic moieties has the purpose of raising the melting temperature of the unsaturated compounds and of their hydrogenated derivatives, so that they are solid at the working temperatures and pressures.

However, a first drawback of the compositions indicated in the last mentioned patents consists in that they are obtained as mixtures of many compounds having different molecular weight. This involves problems in the control and reproducibility of the physical and chemical characteristics of the product. In particular, as it is known, it is difficult to obtain a solution of organic compounds having a very high molecular weight; consequently, the steps for the production of the final getter which require passing through a solution, such as the mixing with the hydrogenation catalyst and the deposition on a porous substrate, are difficult.

A second drawback of the above described composition for hydrogen sorption consists in the high production cost thereof. In facts, the synthesis of the unsaturated compounds or polymers is carried out by a condensation reaction starting from acetylenes and aromatic halides which requires the use of triphenylphosphine and palladium complexes as catalysts. At the end of the reaction, for economical reasons it is necessary to isolate the palladium complex, separating it from the reaction products so that it can be used again. Further, the other catalyst, triphenylphosphine, is a toxic product which should not be used in industrial processes in order to avoid safety and ecological problems.

BRIEF SUMMARY OF THE INVENTION

Therefore, object of the present invention is providing a hydrogen getter composition free from said drawbacks. Said object is achieved by means of a hydrogen getter composition whose main features are specified in the first claim and other features are specified in the subsequent claims.

A first advantage of the hydrogen getter composition according to the present invention consists in that it allows final hydrogen pressures lower than those typical for getters according to the state of the art to be reached with particularly high sorption rates.

A second advantage of the hydrogen getter composition according to the present invention is that its production cost is very low. In fact, the synthesis of the unsaturated organic substances which are the components thereof is carried out from starting materials already available on the market and by means of processes which provide for high yields without using expensive catalysts and do not require subsequent separation steps.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown.

In the drawings:

FIG. 1 is a scheme representing the measuring system used for evaluating the hydrogen sorption properties of the compositions according to the invention; and FIG. 2 is a graph showing the variation of the hydrogen sorption rate as a function of the sorbed hydrogen quantity per gram of unsaturated organic substance a of the getter composition according to the present invention.

DETAILED DESCRIPTION OF THE INVENTION

The hydrogen getter according to the present invention comprises an unsaturated organic substance and a hydrogenation catalyst. The unsaturated organic substance can be a compound having general formula A or A':

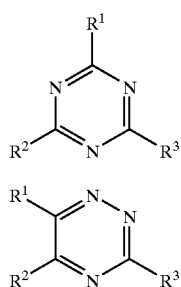

wherein $R^1$, $R^2$ and $R^3$ are hydrogen or hydrocarbon moieties optionally comprising one or more heteroatoms and wherein at least one among $R^1$, $R^2$ and $R^3$ is selected in the group formed of alkenyl, alkynyl, arylalkenyl and arylalkynyl moieties, optionally comprising one or more heteroatoms.

Further, said unsaturated organic substance can be a dimer or a polymer of the compound of general formula A or A', as well as a copolymer wherein one of the structural units has the general formula A or A'.

The three substituents $R^1$, $R^2$ and $R^3$ can be all different from hydrogen and each one can have more than one unsaturated bond, so that the quantity of hydrogen irreversibly sorbed per gram of substance is maximized.

Furthermore, according to a particular embodiment of the present invention the substituents $R^1$, $R^2$ and $R^3$ comprise at least one heteroatom, selected among N, O and S and directly bound to the triazine ring. As a matter of fact it has been found that, contrary to the teachings of U.S. Pat No. 4,405,487, in some cases the presence of the heteroatoms does not affect the reactivity of the compound and the effectiveness of the hydrogenation catalyst. Preferred $R^1$, $R^2$ and $R^3$ substituents are represented by the general formulae R—(C=C)$_n$—CH$_2$—O— and R—(C≡C)$_n$—CH$_2$—O—, wherein $n \geq 1$ and R is any aliphatic or aromatic hydrocarbon moiety.

In order to allow a simplified synthesis of the unsaturated organic substance according to the present invention, in the case of a compound having general formula A or A', the three substituents $R^1$, $R^2$ and $R^3$ are preferably the same.

The compounds of general formula A or A' can be synthesized starting from the corresponding trichlorotriazine according to the following general scheme:

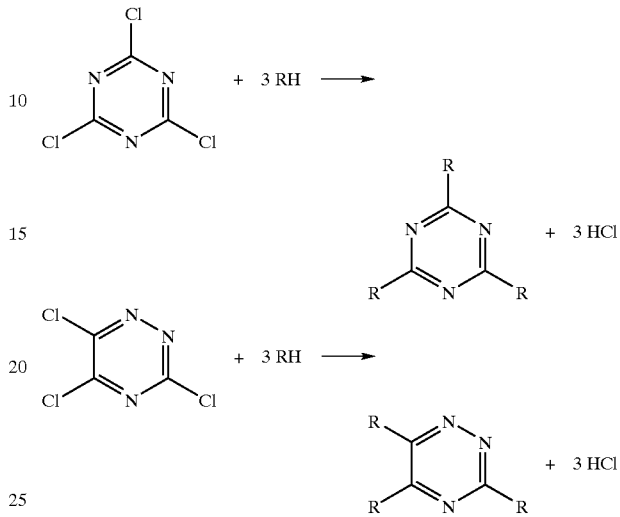

It is important to underline that the above described unsaturated organic substances can be used as the components of a hydrogen getter according to the present invention also in the liquid form, because they generally show good thermal resistance features. However, if the final application of the hydrogen getter involves particularly high working temperatures and solid unsaturated organic substances are required, very high melting points can be obtained by condensing two or more compounds having general formula A or A', so as to obtain dimers or polymers of said compounds. A further possibility consists in condensing two or more molecules of the compound having general formula A or A' with any hydrocarbon compound.

Preferred for the use in the compositions of the invention are the two following organic compounds, both having general formula A:

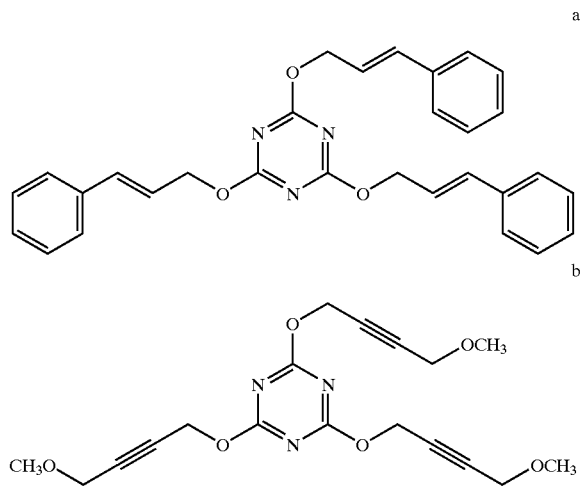

Compound a is a new compound whose name, according to the IUPAC nomenclature, is 2,4,6-tris-(E-3-phenyl-prop-2-enyl-1-oxy)-1,3,5-triazine; this compound has molecular weight of 477,56 g/mol and its melting point has proved to be 128–129° C. This compound may be obtained, for instance, by reacting one equivalent of 2,4,6-trichloro-1,3, 5-triazine with three equivalents of an alkaline metal cinnamate; this latter may be formed in-situ in the reaction medium.

Compound b has the IUPAC name 2,4,6-tris-(4-methoxybut-2-ynyl-1-oxy)-1,3,5-triazine, and molecular weight of 375,38 g/mol.

The catalyst forming part of the getter composition according to the present invention can be any catalyst known in the art for hydrogenation reactions, such as transition metals belonging to Group VIII of the periodic table or salts or complexes thereof. Preferably, palladium supported on alumina or palladium on carbon are used.

Any known technique can be used for obtaining the getter composition according to the present invention. For example, it can be prepared mixing or diluting the unsaturated organic substance in a suitable solvent and adding the hydrogenation catalyst to the obtained solution. After an accurate stirring of the mixture, the getter composition is obtained by evaporation of the solvent. In case of the use of palladium metal as the catalyst, this is preferably present in a quantity ranging between 0,1% and 10% by weight of the unsaturated organic substance.

In the following some examples relevant to the synthesis of organic compounds which can be advantageously used in the getter compositions of the invention, and to the measure of the hydrogen sorption properties of these compositions will be provided.

EXAMPLE 1

This example relates to the synthesis of compound a mentioned in the text.

50 g (0,36 mol) of cinnamic alcohol are dissolved in 180 ml of dry toluene. 20 g (0,36 mol) of KOH are added to the solution, and the resulting mixture is kept under stirring for one hour at room temperature. During this phase, potassium cinnamate is obtained. Then, a solution prepared starting from 18 g (0,10 mol) of 2,4,6-trichloro-s-triazine in 150 ml of toluene is added, allowing to react at room temperature for further 90 hours under stirring.

The reaction mixture is washed with water until pH is neutral. The solution is concentrated and the product is precipitated by addition of diisopropylether. The product is dried and analyzed by NMR and mass spectrometry, which prove it to be 2,4,6-tris-(E-3-phenyl-prop-2-enyl-1-oxy)-1, 3,5-triazine. The compound has melting point of 128–129° C. 37 g of product are obtained, which are equal to a yield of about 78%.

EXAMPLE 2

The synthesis described in example 1 is repeated, but in this case 50 g (0,36 mol) of $K_2CO_3$ are added to the initial mixture of cinnamic alcohol and KOH in toluene. 30 g of 2,4,6-tris-(E-phenyl-prop-2-enyl-1-oxy)-1,3,5-triazine are obtained, with a yield of about 64%.

EXAMPLE 3

This example relates to the synthesis of compound b mentioned in the text.

1,8 g (0,075 mol) of NaH are suspended in 20 ml of tetrahydrofurane (THF) under inert atmosphere. A solution containing 6 g (0,06 mol) of 4-methoxy-but-2-yn-1-ol in 20 ml of THF is added dropwise to the suspension, allowing the reaction to proceed for 3 hours at room temperature under stirring. Then, to this solution is added by slow dripping a solution containing 3,5 g (0,019 mol) of 2,4,6-trichloro-s-triazine in 30 ml of THF allowing to react for one night. The solvent is evaporated and the residue is first washed with 30 ml of water, and then acidificated with a 10% HCl solution. Three subsequent extractions with $CH_2Cl_2$ and evaporation of the solvent are carried out, 6 g of a deep yellow oil are obtained. The product is purified by chromatography on a silica column, using ethyl acetate as eluent. At the end 4,3 g of a yellow liquid are obtained, with a yield of 60%. The final compound is liquid, but it can be impregnated on palladium on carbon obtaining a composition suitable for the purpose of the invention, which has a null vapor pressure in the hydrogen sorption test.

EXAMPLE 4

This example relates to the measure of the hydrogen sorption capacity of a composition according to the invention containing compound a.

For this measure the system diagrammatically shown in FIG. 1 is used, formed of a hydrogen reservoir 10, connected by means of a needle valve 11 to a chamber 12 having known volume, whose pressure is measured by means of a capacitive manometer 13; chamber 12 is connected by means of valve 14 to a pumping system (not shown in the figure). Furthermore, chamber 12 is connected, by means of a liquid nitrogen trap 15 and a valve 16, to measuring chamber 17; this latter chamber is connected in turn to a pumping system (not shown in the figure) by means of valve 18. Trap 15 has the purpose of blocking the passage of possible impurities from chamber 12 to chamber 17.

10 g of compound a prepared as described in example 1 are dissolved in 50 ml of ethyl alcohol. 10 g of 5% palladium on carbon of the company Aldrich are added to the solution; this material consists in carbon powder having a high specific surface on which palladium in metal form has been deposited in a quantity of 5% by weight of the sum of carbon and Pd. The obtained solution is stirred for half an hour, and subsequently the solvent is eliminated by evaporation, thus obtaining a residue formed of a mixture of compound a and palladium on carbon.

1 g of the mixture is introduced, in the powder form, in measuring chamber 17. Chamber 17 is evacuated to a pressure of $1,33 \times 10^{-3}$ mbar, then the chamber is isolated from the pumping by closing valve 18. With valve 16 closed, valve 11 is opened until the pressure in the system has reached the value of 6,7 mbar. Now, valve 16 is opened and valve 11 is closed, while the pressure decrease in the system due to the sorption by the sample under analysis is measured. When the pressure is decreased to one tenth of the initial value (0,67 mbar) the procedure for the hydrogen dosage is repeated. The same procedure is repeated until when, after the introduction of hydrogen in the measuring chamber, no sorption by the sample is detected. The pressure values as a function of the testing time are processed, thus obtaining sorption rate values (S) as a function of the sorbed hydrogen quantity (Q) by means of the following formulae:

$$Q_i = (P_0 - P_1) \times V$$

$$S_i = -V/P_1 \times (dP/dt)$$

wherein $Q_i$ is the quantity of hydrogen sorbed at time i, $S_i$ the volumetric sorption rate at time i, $P_0$ the initial pressure, $P_i$ the pressure at time i, V the total volume of the measuring system.

Q and S are then normalized with respect to the weight of the getter sample. The results of the test are given in FIG. 2.

As it can be seen from the figure, the composition containing compound a sorbs a total quantity of about 67 (mbar×1/g) of hydrogen, equivalent to about 133 (mbar×1/g) if referred to compound a alone; the sorption rate varies from an initial value of about $5{,}3\times10^{-3}$ (mbar×1/g×s) to a value of about $2{,}7\times10^{-5}$ (mbar×1/g×s) when the sorption capacity of the composition is almost exhausted.

EXAMPLE 5

The test of example 4 is repeated on a sample of one gram of composition of the invention, obtained impregnating 0,5 g of compound b produced as described in example 3 on 0,5 g of 5% palladium on carbon. This composition shows a hydrogen sorption capacity of 186 (mbar×1/g) if referred to compound b alone, with sorption speed equal to $2{,}7\times10^{-3}$ (mbar×1/g×s) at the beginning of the test and $8\times10^{-6}$ (mbar×1/g×s) at the end thereof.

Possible variations and additions can be made by those which are skilled in the art to the hereby described and illustrated embodiment remaining within the scope of the invention itself.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. An unsaturated organic substance having formula:

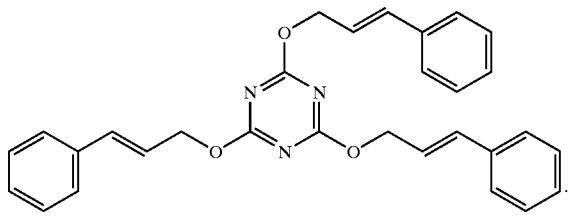

2. A process for the synthesis of the organic substance according to claim 1, characterized in that 2,4,6-trichloro-1,3,5-triazine is reacted with three equivalents of an alkaline metal cinnamate.

3. A hydrogen getter composition comprising the unsaturated organic substance according to claim 1 and a hydrogenation catalyst.

4. The hydrogen getter composition according to claim 3, wherein the hydrogenation catalyst is selected from the group consisting of metals of Group VIII of the periodic table, salts and complexes thereof.

5. The hydrogen getter composition according to claim 4, wherein the hydrogenation catalyst is palladium supported on alumina or carbon.

6. The hydrogen getter composition according to claim 5, wherein palladium is present in an amount of 0.1% to 10% by weight of the unsaturated organic substance.

* * * * *